(12) United States Patent
Pohlman et al.

(10) Patent No.: US 10,874,119 B2
(45) Date of Patent: Dec. 29, 2020

(54) PILL AND PASTE CARRIER

(71) Applicant: Standlee Hay Company, Inc., Kimberly, ID (US)

(72) Inventors: Nancy L. Pohlman, Camp Verde, AZ (US); Timothy J. Pearl, Twin Falls, ID (US); Stephen E. Duren, Weiser, ID (US); Jason G. Egbert, Murtaugh, ID (US); Manase M. Ngauamo, Murtaugh, ID (US); Kathleen F. Starr, Hazelton, ID (US); Brook K. Bacon, Twin Falls, ID (US)

(73) Assignee: Standlee Hay Company, Inc., Kimberly, ID (US)

(*) Notice: Subject to any disclaimer, the term of this patent is extended or adjusted under 35 U.S.C. 154(b) by 172 days.

(21) Appl. No.: 16/141,860

(22) Filed: Sep. 25, 2018

(65) Prior Publication Data

US 2019/0021369 A1  Jan. 24, 2019

Related U.S. Application Data

(63) Continuation-in-part of application No. 15/170,761, filed on Jun. 1, 2016, now abandoned.

(51) Int. Cl.
| | |
|---|---|
| *A61K 9/00* | (2006.01) |
| *A23K 40/30* | (2016.01) |
| *A23K 40/20* | (2016.01) |
| *A23K 30/12* | (2016.01) |
| *A61K 47/46* | (2006.01) |
| *A23K 50/42* | (2016.01) |
| *A23K 10/33* | (2016.01) |
| *A23K 50/20* | (2016.01) |
| *A23K 50/40* | (2016.01) |
| *A23K 20/163* | (2016.01) |
| *A23K 50/10* | (2016.01) |
| *A61K 9/107* | (2006.01) |
| *A23K 20/158* | (2016.01) |

(52) U.S. Cl.
CPC ............ *A23K 40/30* (2016.05); *A23K 10/33* (2016.05); *A23K 20/158* (2016.05); *A23K 20/163* (2016.05); *A23K 30/12* (2016.05); *A23K 40/20* (2016.05); *A23K 50/10* (2016.05); *A23K 50/20* (2016.05); *A23K 50/40* (2016.05); *A23K 50/42* (2016.05); *A61K 9/0056* (2013.01); *A61K 9/107* (2013.01); *A61K 47/46* (2013.01)

(58) Field of Classification Search
None
See application file for complete search history.

(56) References Cited

U.S. PATENT DOCUMENTS 3,996,848 A * 12/1976 Molitorisz ............ B30B 11/222
100/73

* cited by examiner

*Primary Examiner* — Susan T Tran
(74) *Attorney, Agent, or Firm* — Richard D. Clarke

(57) ABSTRACT

The present invention is directed to a forage-based Pill and Paste Carrier for feeding to horses, donkeys, livestock and pets. More particularly, the Pill and Paste Carrier is formed into a hollow cylinder or disk shape, and can accept and hold a pill, a semi-solid or a liquid, or be filled with a paste. Provided is a method for making a Pill and Paste Carrier by formulation of a forage-based mixture, including a binder and a flavor enhancing substance, as well as any additive to promote animal health, then pressing and drying the formed hollow cylinder or disk and optionally filling with a formulated paste. Further provided is a method of administering medications to healthy animals or animals with acute or chronic health issues, who often make this process very difficult.

20 Claims, 10 Drawing Sheets

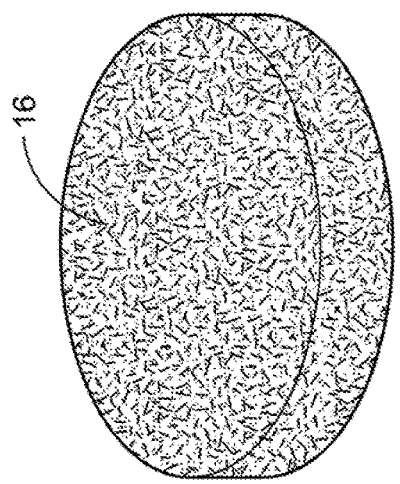
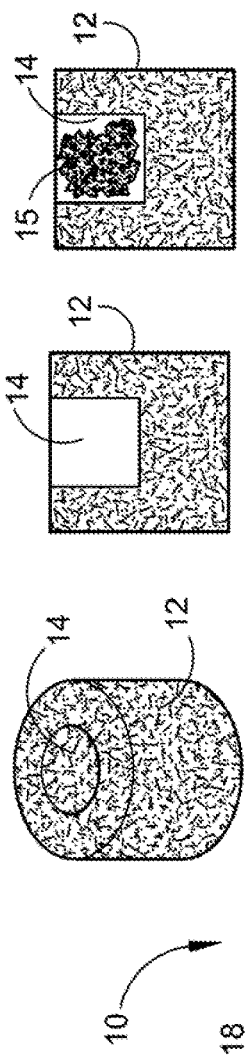
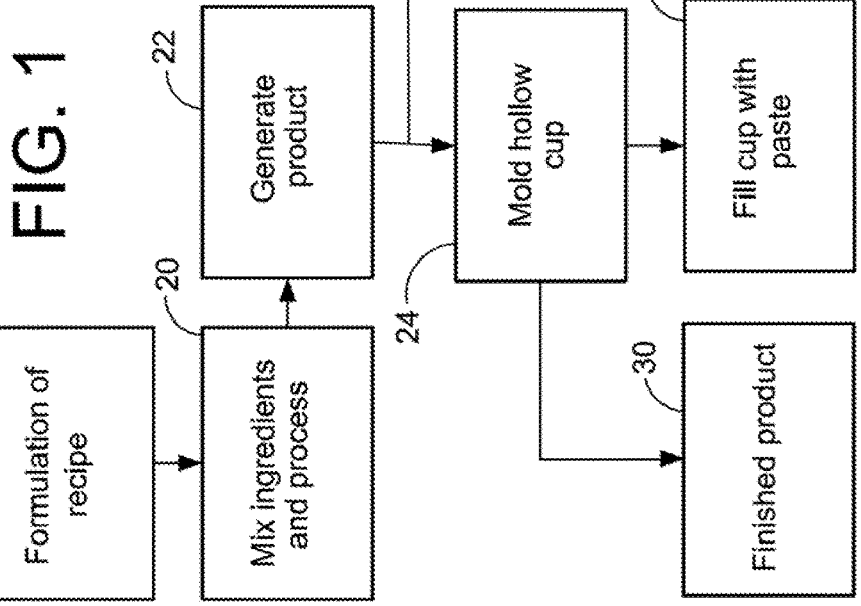

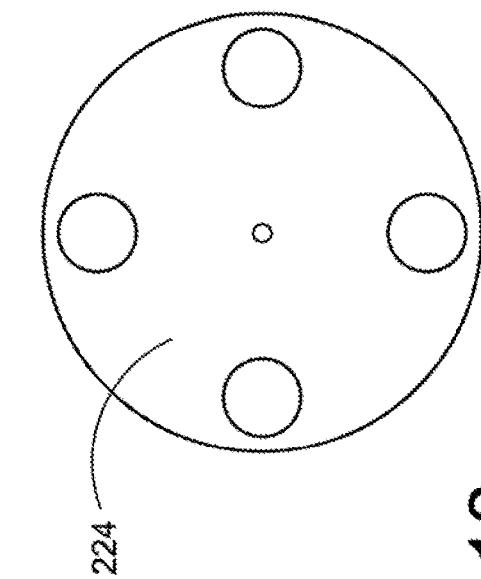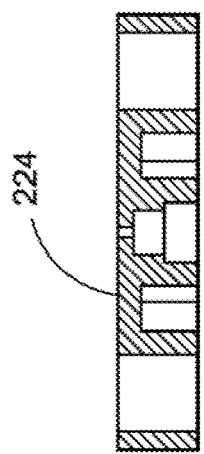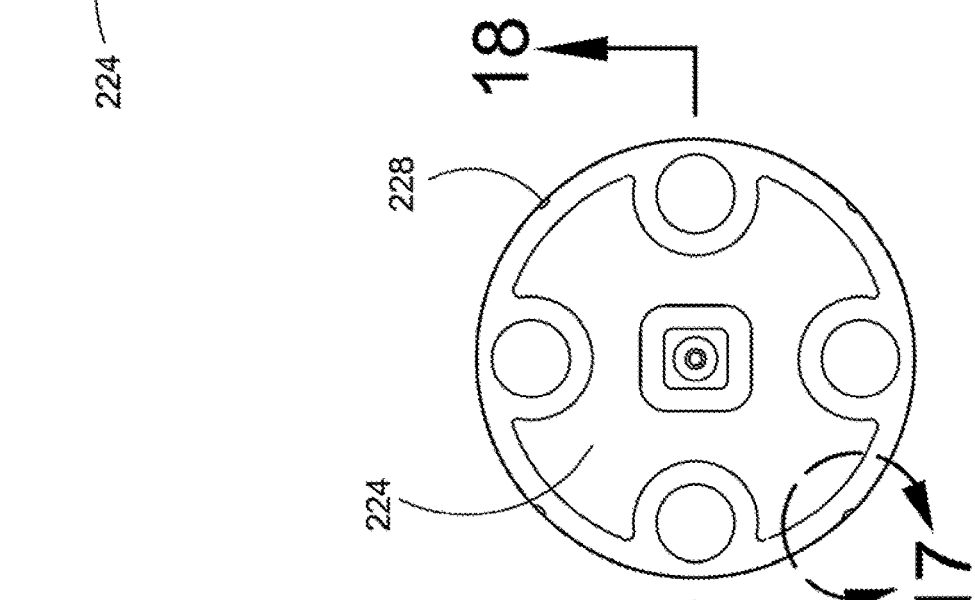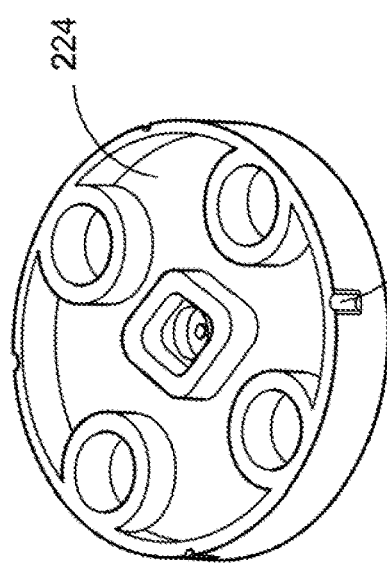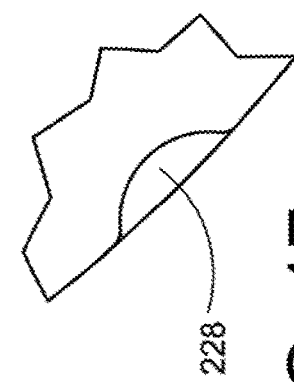

PILL AND PASTE CARRIER

FIELD OF THE INVENTION

Provided is a forage-based Pill and Paste Carrier for feeding to horses, donkeys, livestock and pets. More particularly, the Pill and Paste Carrier is formed into a hollow cylinder or disk shape, and can accept and hold a pill, a semi-solid or a liquid, or be filled with a paste. Provided is a method for making a Pill and Paste Carrier by formulation of a forage-based mixture, including a binder and a flavor enhancing substance, as well as any additive to promote animal health, then pressing and drying the formed hollow cylinder or disk and optionally filling with a formulated paste. Further provided is a method of administering medications to healthy animals or animals with acute or chronic health issues, who often make this process very difficult.

BACKGROUND OF THE INVENTION

Forage, such as hay and pasture is critical for the health and well-being of all horses. Understanding the design, function and reliance of the horse's digestive system on forage is the first step in appreciating the critical value of forage. Knowledge of what's in forage, the types and physical forms of forage and importance of forage quality should be common for all horse owners. Finally, understanding how much forage a horse requires per day is essential in properly feeding any horse. So let's get started learning about forages for horses.

The unique structure and function of the horse's digestive system is ideally suited for the utilization of forage. As such, horses are classified as herbivores or plant eaters. They are also referred to as "hindgut fermenters" since the back portion of the digestive tract is a large fermentation vat. The horse's hindgut is a large balloon-like area consisting of the cecum and colon. It is the largest area of the digestive system making up over 65% of the digestive capacity. Billions of bacteria and protozoa live in this portion of the digestive tract. These microorganisms work together to break down (ferment) plant fiber from forage. It is the presence of these microorganisms in the hindgut that allows horses to utilize forage. Without these microorganisms the horse would not be able to digest forage. The intestinal microorganisms produce energy-yielding compounds called volatile fatty acids, as well as amino acids and B-vitamins that can be absorbed by the horse.

With over 65% of the horse's digestive system geared towards digestion of forage, it is easy to see why forage is critical to the health of all horses.

Forage comes in many different types and physical forms. In general, forages can be divided into two types: legumes and grasses.

Legumes are plants such as alfalfa and clover. They are capable of fixing their own nitrogen and therefore they have higher protein content. Legumes also contain less fiber and more of that fiber is un-digestible fiber compared to grasses.

Grasses that are fed to horses include many different species. The individual species of grass are further divided into those which grow well in colder climates—cool season grasses (e.g. ryegrass, orchard, timothy, and prairie) and those that grow well in hotter climates—warm season grasses (e.g. Bermuda, kikuyu and Pangola). Again, grasses typically contain less protein and more fiber compared to legume forages.

The physical form of forages fed to horses is also quite variable. The simplest form of forage is pasture. Pasture can contain both grass and legume plants. Pasture plants can be selected to grow in all types of climates. Unfortunately when conditions become harsh such as during extreme heat or cold, pasture plants will quit growing and become dormant. At these times of the season, the horse must rely on physical forms of forage that have been stored.

Hay is the most common form of stored forage. To make hay, plants are grown to a certain height or maturity, cut, dried to low moisture content and packaged into a bale. If the moisture content is greater than 12% the hay will mold while in storage. Feeding moldy forage is never recommended with horses since it can result in digestive upset (colic) or even death. Forage that has been stored initially as hay can then be further processed into other physical forms. These forms include pellets, cubes, or chaff. These physical forms of forage have the same digestibility as the hay they were made from. The processing into pellets, cubes or chaff simply add convenience in handling or feeding. Processing hay into cubes or pellets also allows hay to be readily transported from areas with favorable hay growing conditions to areas of the country with poor hay growing conditions. Pelleted or cubed forages are also the correct choice for aged horses or horses with poor teeth. Pellet and cubes can be soaked in water to form a mash or gruel that is well tolerated by these "special needs" horses.

The main factors that influence the quality of forage are: specie of plant, stage of maturity of the plant and the physical location where the plant was grown. As mentioned previously, legume plants (alfalfa and clover) tend to be higher in protein, energy and calcium compared to grass plants. Hence, legume forages are best suited for horses with elevated nutrient requirements such as broodmares and growing horses. On the other hand, grass forages because of the lower energy content may be better suited to horses that gain weight easily or for show horses.

The maturity of the plant is also a determinant of forage quality. The more mature a plant becomes or the taller a plant grows, the lower the quality. As plants mature, digestibility decreases due to an increased amount of fiber to keep the plant upright. Due to the high fiber content of mature plants, they proportionally contain less energy, protein, vitamins and mineral compared to shorten, less mature plants. Hay that is cut when the plants are too tall and mature will be less digestible. The cutting of hay is often delayed in many geographic areas of the country due to rain or poor weather. These weather delays decrease the quality of hay.

The final determinant of forage quality is the physical location where the plant was grown. Different geographic regions contain soils with different nutrient densities. The nutrient content of the soil is reflected in the nutrient content of the plant. For example, plants grown in nutrient deficient soil will also be nutrient deficient and of lower quality. As mentioned previously, certain areas of the country have difficulty in growing quality forage because of poor climate conditions. Forage grown in the Western United States is some of the highest quality in the world because of optimum growing and harvesting conditions.

Forage quality can be determined to a limited extent by visual inspection of the forage. Visual inspection can include looking at: the leaf to stem ratio, the length of the seed head, color of the plant, and the presence of dust or mold.

Higher quality forages will have more leaves than stems, a short seed head, be green in color, and smell fresh with no dust or mold. A more accurate evaluation of forage quality can be acquired via a laboratory analysis. First, a representative sample of forage is sent to the laboratory for chemical analysis. The results will then provide accurate determination of energy, protein, vitamin and mineral content. Laboratory analysis can also be used to determine the presence of harmful mold.

Forage is the safest dietary ingredient that can be fed to horses. Horses require an absolute minimum of 1.5-2.5% of their body weight in dry forage per day, for a 1000 lb. horse this equates to just 15-25 lbs. of forage per day. Racehorses are the only horses that would get down to this minimum amount of forage. A safer guideline is to provide horses with a minimum of 2.0% of their body weight in dry forage per day, which equates to 20 lbs. of dry forage per day for a 1000 lb. horse. So how much forage will a horse eat? Conservative estimates are for horses to consume a maximum of 3.5% of their body weight in dry forage per day. This is a whopping 35 lbs. of dry forage per day for a 1000 lb. horse.

Forage is the most important dietary ingredient for horses. The digestive system of the horse is designed to digest forage. There are many types and physical forms of forage. All forages fed to horses should be of good quality. Forage should be offered free-choice to horses unless your horse is obese or somehow sensitive to something in forage. Feeding large volumes of forage will maximize digestive health and minimize the amount of grain that will need to be provided to the horse.

Forage contains all of the essential nutrients required by horses: water, energy, protein, vitamins and minerals. Unfortunately, many horse owners only talk about, or judge forage based on protein content. While protein is certainly important, other nutrients are often as important. Forage should be judged by the levels of all nutrients not by any one single nutrient. The following are some of the nutrients that forage contains along with a brief explanation.

Water—Pasture contains large amounts of water whereas preserved forages such as hay, hay cubes or pellets and chaff have been dried to prevent mold growth while in storage.
   Protein—The protein content is highest in legumes such as alfalfa and clover and lower in grasses such as timothy or orchard grass.
   Fat—Forage contains a small amount of fat which is high in omega 3 fatty-acids.
   Fiber—Not all of the fiber in forages is digestible with an overall estimate of digestibility ranging from 40 to 50%. As bay becomes more mature (taller), the fiber content increases and the digestibility decreases.
   Minerals—A number of important minerals such as calcium, phosphorus, potassium, copper, zinc, selenium and others are present. The mineral content of forage is dependent on soil conditions where the plants were grown.
   Vitamins—The vitamin content of green forages is higher compared to sun-bleached or weather-damaged forage.

Good quality forage is important for horses. During times when pasture is not available, such as after a drought or wildfire, the selection and purchase of hay or other forage sources becomes a vital decision for horse owners. The quality and nutrient content of the hay or forage source is critical because it is the foundation of the horse's diet and provides 50 to 90% of the total nutrient intake for many horses.

Why should horse owners be concerned about forage sources for their horses? Due to the horse's unique and delicate digestive system, it needs to consume a minimum of 1% of its body weight daily (dry matter) as forage in the form of hay, chaff, and pasture together with some grain.

Most horses are fed more than that amount, receiving 2% of their body weight per day in grass or hay alone. This means that a 450 kg (1,000 lb.) horse will easily eat 5 to 7 kg (1 to 15 lb.) of forage per day, along with 1.5 to 3 kg (3.3 to 6.6 lb.) of a grain ration in order to maintain a healthy digestive system and good body condition. For lactating mares or young growing horses, hay consumption is much higher and can be as much as 3% of body weight.

When problems occur that may relate back to nutrition, people usually look at the grain ration. However, when the vast majority of the horse's diet is hay or grass, we must pay more attention to the important role that hay, or another forage plays in the horse's nutritional status.

Several factors affect the quality, and therefore the nutrient content, of hay. These include plant species, fertilization, maturity at time of harvest, rain and sun when hay is harvested, climatic conditions, storage conditions, and age (time since cutting). The maturity of the plant at time of harvest determines the hay quality more than any other factor.

Legume hays such as alfalfa or clover have higher protein, energy, and calcium contents than grass or cereal hays. They are also usually more palatable and often a better value. Hay for horse consumption should be baled from grass that is in early maturity. The hay should have been allowed adequate curing time, and ideally was baled and stored without being rained on. If the hay was baled too green or was rained on, there will often be mold within the bale. This may be detected by smell or discoloration of stems. If hay gets wet after cutting, it can be dried to avoid mold, but often the stems are discolored, and a lot of the sugar and energy are washed out of it. When certain types of mold are consumed by the horse, serious complications such as colic can arise.

After drying, some hay is very dusty. This is often more of a health risk than mold. Every time a horse buries its nose in dusty hay or picks up a piece and shakes it, there is a cloud of dust. Continuously breathing in dust at such close range will quickly lead to lung problems. The short term effect is acute pneumonia, with difficult breathing and coughing. The chronic effects are those seen with the condition of heaves or emphysema. This condition can be managed with medication, but never cured. If dusty hay is all you have, soaking the hay will keep the dust down but will also wash out some of the sugar and energy.

Most people buy hay based on how it looks, smells, and feels. These are qualitative factors, and they are important. When appraising hay, keep in mind the following points:
   It's what's inside that counts. Ask that one or several bales be opened so you can evaluate the hay inside the bales. Do not worry about slight discoloration on the outside, especially in stacked hay.
   Choose hay that is as fine-stemmed, green, leafy, and soft to the touch as possible.
   Avoid hay that is excessively bleached or discolored, or that smells moldy, musty, dusty, or fermented.
   Check for leaf loss. If the leaves of alfalfa or clover hay fall too easily off the stems, the horse won't be able to eat them.
   Examine the leaves, stems, and flowers or seed pods to determine the level of maturity.
   Select hay that has been baled when the plants are in early bloom (for legumes) or preferably before seed heads have fully formed in grasses.
   Avoid hay that contains significant amounts of weeds, dirt, trash, or debris.
   Some cereal hays such as barley and triticale hay can have sharp awns if cut and baled when too mature.
   Examine hay for signs of insect infestation or disease. Be especially careful to check for insects in alfalfa.

Reject bales that seem excessively heavy for their size or feel warm to the touch. They may contain excess moisture that could cause mold or spontaneous combustion.

When possible, feed hay within a year of harvest to guarantee the best nutritional value.

Store hay in a dry, sheltered area, or cover the stack to protect it from the elements. Allow some air circulation when covering with plastic or tarps.

Try to feed hay in a way that reduces wastage. Hay feeders or nets are very useful.

If hay isn't available, you can feed high fiber feeds that contain a large percentage of chaff. Look at the crude fiber level as a guide.

Remember that hay can make up a large part of the horse's diet when pasture is limited or nonexistent. If you are working your horses, they will usually need some added grain. Key visual and physical inspection factors include a fresh, clean smell and freedom from dust or mold. If in doubt about the quality of hay, don't feed it!

With the advent of the present invention by Standlee Premium Western Forage, giving pills to horses, livestock and pets just got easier. Standlee Premium Western Forage has developed a medicine carrier for your horses that is a tasty treat and easy to use. Standlee Pill and Paste Carriers assist with providing oral medications or supplements to your horse, pony or donkey, or other livestock and pets.

As pet, horse and other livestock owners know too well, giving oral medications to horses can be an arduous task. Pastes are a little easier than other oral medications, often with a long syringe that can be placed toward the rear of the horse's mouth. Pills however, can be very difficult to administer to our horses.

Owners often grind the pills and try to mix them into the feed. A picky eater will repeatedly sift through the feed making sure not to consume any of the ground pills. Yet, you can't stop trying. Your horse must get the total dose of medicine at the correct time for the prescribed number of days. Standlee Premium Western Forage has been very busy developing an easier solution for giving medication to your favorite pet, livestock or horse. Standlee Pill and Paste Carriers assist significantly with providing oral medications or supplements to your pet, livestock, horse, pony or donkey. These pill carriers are a much-needed answer to medication delivery, through a nutritious forage-based treat.

Features and Benefits

Premium Quality Alfalfa-Based—natural option for dispensing medication in pill or paste form Hollow Cylinder Design with "Pill Holding" Technology—prevents pill from falling out of the cylinder Safe to Feed—Horse pill carriers can be fed empty as a treat to eliminate potential horse refusal Stay Fresh Packaging—re-sealable package to keep horse pill carriers fresh and palatable.

Standlee Premium Western Forage Pill Carriers are naturally flavored with fenugreek seed. Researchers in England studied the top flavors selected by horses, and fenugreek, banana and cherry topped the list. Analysis of the final data showed that the top eight flavors were, in order of preference, fenugreek, banana, cherry, rosemary, cumin, carrot, peppermint and oregano. See the reference: Goodwin, D., Selection and acceptance of flavours in concentrate diets for stabled horses, Applied Animal Behaviour Science, Volume 95, Issue 3, Pages 223-232, December 2005.

Standlee Premium Western Forage has very consistent products, which is also extremely important when trying to administer a medication. We want to make sure the horse is readily consuming the pill carriers void of any medications, so that horses view them as a treat. The alfalfa base and fenugreek flavoring then continue to mask the flavor of the medication you are providing. Additionally, the forage in Standlee's Horse Pill Carriers is not super finely chopped; the fiber length offers a normal texture to the horse and also covers the texture of any medication you might be providing. With the preferred formulations used as a way to introduce agents having a positive bodily effect, the following pills, agents or liquids can be readily delivered using the hollow cylinder style Pill and Paste Carrier, or the disk style Pill and Paste Carrier: medications of all kinds, probiotics, pre-biotics, psyllium, anti-diuretics, biotin, anti-oxidants, antibiotics, electrolytes, omega-3, DHA and EPA, bone health agents, hoof and coat health agents, fly and pest supplements, vitamins and minerals, digestive health agents, joint health agents, feed supplements, CBD (cannabidiol), herbs, hemp, over-the-counter sedatives, and peanut butter paste, to name a few. Being able to have your pet, livestock, horse, or donkey take these medicines and agents will have a significant bodily effect on the animal and the health and wellness of the animal will be greatly enhanced.

Numerous innovations for the making and conveying medications to animals have been provided in the prior art that are described as follows. Even though these innovations may be suitable for the specific individual purposes to which they address, they differ from the present design as hereinafter contrasted. The following is a summary of those prior art patents most relevant to this application at hand, as well as a description outlining the difference between the features of the Pill and Paste Carrier and the prior art.

US Patent Application Publication No. US 2017/0020162 A1 of Laura Gill Martens describes an invention relating to a mixture for making a cooking-extruded extrudate, the mixture including an aqueous animal ensilage and a vegetable material, and—the aqueous animal ensilage including a water-soluble protein fraction, a water-insoluble protein fraction and fat;—the mixture including from 12.5% by weight or more of ensilage dry matter to 42% by weight or less of ensilage dry matter; and—the mixture including at least 15% by weight of water and less than 34% by weight of water. The invention also relates to a method of making a cooking-extruded extrudate from the mixture. The invention further relates to a use of the cooking-extruded extrudate.

This patent describes a number of varying recipes for products used in animal husbandry but does not offer the unique method and product for concealing the application within a product that will be very desirable to the animal as the Pill and Paste Carrier method.

US Patent Application Publication No. US 2017/0202244 A1 of David Calabotta et al. discloses and invention comprising embodiments of compositions and combinations that can be used in combination with animal food. In some embodiments, the combinations comprise various compositions that can provide health benefits for animals, such as domestic or companion animals and/or feed animals. The combinations can be used to help maintain and/or promote animal health and well-being, and in some embodiments can help promote an increase in animal longevity.

This is another patent that describes a number of varying recipes for products used in animal husbandry but does not offer the unique method and product for concealing the application within a product that will be very desirable to the animal as the Pill and Paste Carrier method.

None of these previous efforts, however, provides the benefits attendant with the Pill and Paste Carrier. The present design achieves its intended purposes, objects and advantages over the prior art through a new, useful and unobvious combination of method steps and component elements, with the use of a minimum number of functioning parts, at a reasonable cost to manufacture, and by employing readily available materials.

In this respect, before explaining at least one embodiment of the Pill and Paste Carrier in detail it is to be understood that the fabrication or equipment design is not limited in its application to the details of construction and to the arrangement, of the components set forth in the following description or illustrated in the drawings. The Pill and Paste Carrier is capable of other embodiments and of being practiced and carried out in various ways. In addition, it is to be understood that the phraseology and terminology employed herein are for the purpose of description and should not be regarded as limiting. As such, those skilled in the art will appreciate that the conception, upon which this disclosure is based, may readily be utilized as a basis for designing of other structures, methods and systems for carrying out the several purposes of the present application. It is important, therefore, that the claims be regarded as including such equivalent construction insofar as they do not depart from the spirit and scope of the present application.

SUMMARY OF THE INVENTION

The principle advantage of the Pill and Paste Carrier is a method to give animals, especially horses, medications that are concealed in a flavorful container. With the preferred formulations the following pills, agents or liquids can be readily delivered using the hollow cylinder style Pill and Paste Carrier, or the disk style Pill and Paste Carrier: medications of all kinds, probiotics, pre-biotics, psyllium, anti-diuretics, biotin, anti-oxidants, antibiotics, electrolytes, omega-3, DHA and EPA, bone health agents, hoof and coat health agents, fly and pest supplements, vitamins and minerals, digestive health agents, joint health agents, feed supplements, CBD (cannabidiol), herbs, hemp, over-the-counter sedatives, and peanut butter paste, to name a few. Being able to have your pet, livestock, horse, or donkey take these medicines and agents will have a significant bodily effect on the animal and the health and wellness of the animal will be greatly enhanced.

The principle advantage of the Pill and Paste Carrier is that they will conceal either a pill or paste style of medication or nutritious and health benefiting supplements.

Another advantage is getting the animals accustomed to receiving similar products whether they have the medication in them or not, as in the routine or daily feeding of a treat.

Another advantage of the Pill and Paste Carrier is that they can be used on a wide variety of similar types of animals including those on farms, ranches and in zoos.

Another advantage of the Pill and Paste Carrier is that they can be manufactured in a wide variety of sizes.

Another advantage of the Pill and Paste Carrier is that they can be manufactured using different medications and products suitable for a specific animal health and nutrition needs.

Another advantage of the Pill and Paste Carrier is that it can be used by a veterinarian as a drug delivery system and a veterinarian can adjust the amount of medication that is needed for a specific animal needs.

These together with other advantages of the Pill and Paste Carrier, along with the various features of novelty, which characterize the design, are pointed out with particularity in the claims annexed to and forming a part of this disclosure.

For a better understanding of the Pill and Paste Carrier, its operating advantages and the specific objects attained by its uses, reference should be made to the accompanying drawings and descriptive matter in which there are illustrated preferred embodiments of the Pill and Paste Carrier. There has thus been outlined, rather broadly, the more important features of the design in order that the detailed description thereof that follows may be better understood, and in order that the present contribution to the art may be better appreciated. There are additional features of the Pill and Paste Carrier that will be described hereinafter, and which will form the subject matter of the claims appended hereto.

While the apparatus and method has or will be described for the sake of grammatical fluidity with functional explanations, it is to be expressly understood that the claims, unless expressly formulated under 35 USC 112, or similar applicable law, are not to be construed as necessarily limited in any way by the construction of "means" or "steps" limitations, but are to be accorded the full scope of the meaning and equivalents of the definition provided by the claims under the judicial doctrine of equivalents, and in the case where the claims are expressly formulated under 35 USC 112 are to be accorded full statutory equivalents under 35 USC 112, or similar applicable law. The invention can be better visualized by turning now to the following drawings wherein like elements are referenced by like numerals.

BRIEF DESCRIPTION OF THE DRAWINGS

The accompanying drawings, which are incorporated in and form a part of this specification, illustrate embodiments of the Pill and Paste Carrier and together with the description, serve to explain the principles of this application.

FIG. 1 depicts a perspective view of one of the hollow cylinder cup style of Pill and Paste Carrier.

FIG. 2A depicts a cross section through one of the hollow cylinder cup style Pill and Paste Carrier.

FIG. 2B depicts a cross section through one of the hollow cylinder cup style Pill and Paste Carrier, showing the paste filling within the hollow cylinder.

FIG. 3 depicts a perspective view of the disk style of Pill and Paste Carrier.

FIG. 4 depicts a block diagram of a brief description of the initial production method.

FIG. 14 depicts a perspective bottom view of the rotating disk style Pill and Paste Carrier psyllium wheel.

FIG. 15 depicts a plan view of the bottom of the rotating disk style Pill and Paste Carrier psyllium wheel.

FIG. 16 depicts a plan view of the top of the rotating disk style Pill and Paste Carrier psyllium wheel.

FIG. 17 depicts a section view of the rotating disk style Pill and Paste Carrier psyllium wheel at one of the rotational indexing indentions.

FIG. 18 depicts a cross section of the rotating disk style Pill and Paste Carrier psyllium wheel.

Figure 5:
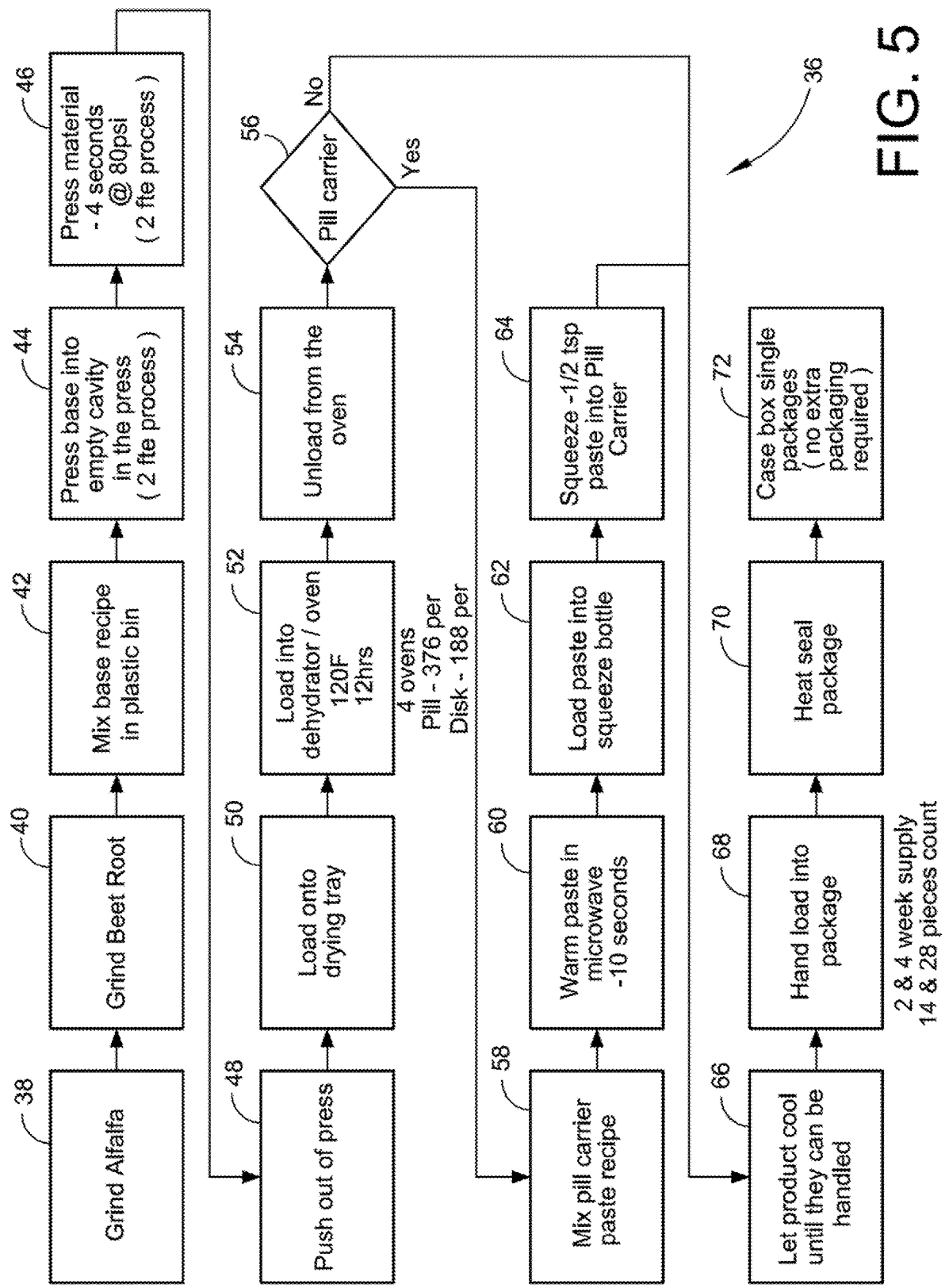
FIG. 5 depicts a block diagram of the first production method.

For a fuller understanding of the nature and advantages of the Pill and Paste Carrier, reference should be had to the following detailed description taken in conjunction with the accompanying drawings which are incorporated in and form a part of this specification, illustrate embodiments of the design and together with the description, serve to explain the principles of this application.

DETAILED DESCRIPTION OF THE PREFERRED EMBODIMENTS

Referring now to the drawings, wherein similar parts of the Pill and Paste Carrier 10 are identified by like reference numerals, there is seen in FIG. 1 a perspective view of one of the Cup style of Pill and Paste Carrier 12 that is approximately one inch wide and one inch high with a central cavity 14 one half inch diameter and three quarters of an inch deep.

FIG. 2A depicts a cross section through one of the cup style of Pill and Paste Carrier 12 further illustrating the depth of the central cavity 14.

FIG. 2B depicts a cross section through one of the cup style of Pill and Paste Carrier 12 further illustrating the depth of the central cavity 14, and showing the paste filling within the hollow cylinder Pill and Paste Carrier 12.

FIG. 3 depicts a perspective view of the Disk style of Pill and Paste Carrier 16 that is approximately one and one half inches in diameter and one half to three quarters of an inch thick.

FIG. 4 depicts a block diagram of a brief description of the initial production method where the Formulation of the Recipe 18 and the Mix ingredients and process 20. The generate product 22 and Mold the hollow cup 24 or Molding the disk 26 where it is moved to the Finished product 28. After Molding the hollow cup 24, the material is transferred to the Finished product 30 or to Fill cup with paste 32 and then to the Finished product 34.

FIG. 5 depicts a block diagram of the First production method 36 where Grind alfalfa 38 with Grind beet root 40, then Mix base recipe in plastic bin 42 and Press base into empty cavity in the press (2 fte process) 44, then Press material—4 seconds @ 80 psi (2 fte process) 46. Next Push out of press 48 and Load into drying tray 50, Load into dehydrator/oven—120 F for 12 hrs 52 (4 ovens—Pill—376 per/Disk—188 per). Optionally, a convention oven may be used at 225 F for 2 hrs. to dehydrate product loaded onto the drying tray. Unload from oven 54 to Pill carrier 56, YES to Mix pill carrier paste recipe 58 then to Warm paste in microwave—10 seconds 60 and Load paste into squeeze bottle 62 then Squeeze—½ tsp paste into pill carrier 64 then connect from the NO line from pill carrier 56 to Let product cool until they can be handled 66 and Hand load into package 68 (2 & 4 week supply/14 & 28 pieces count). Heat seal package 70 and then Case box single packages (no extra packaging required) 72.

Figure 6:
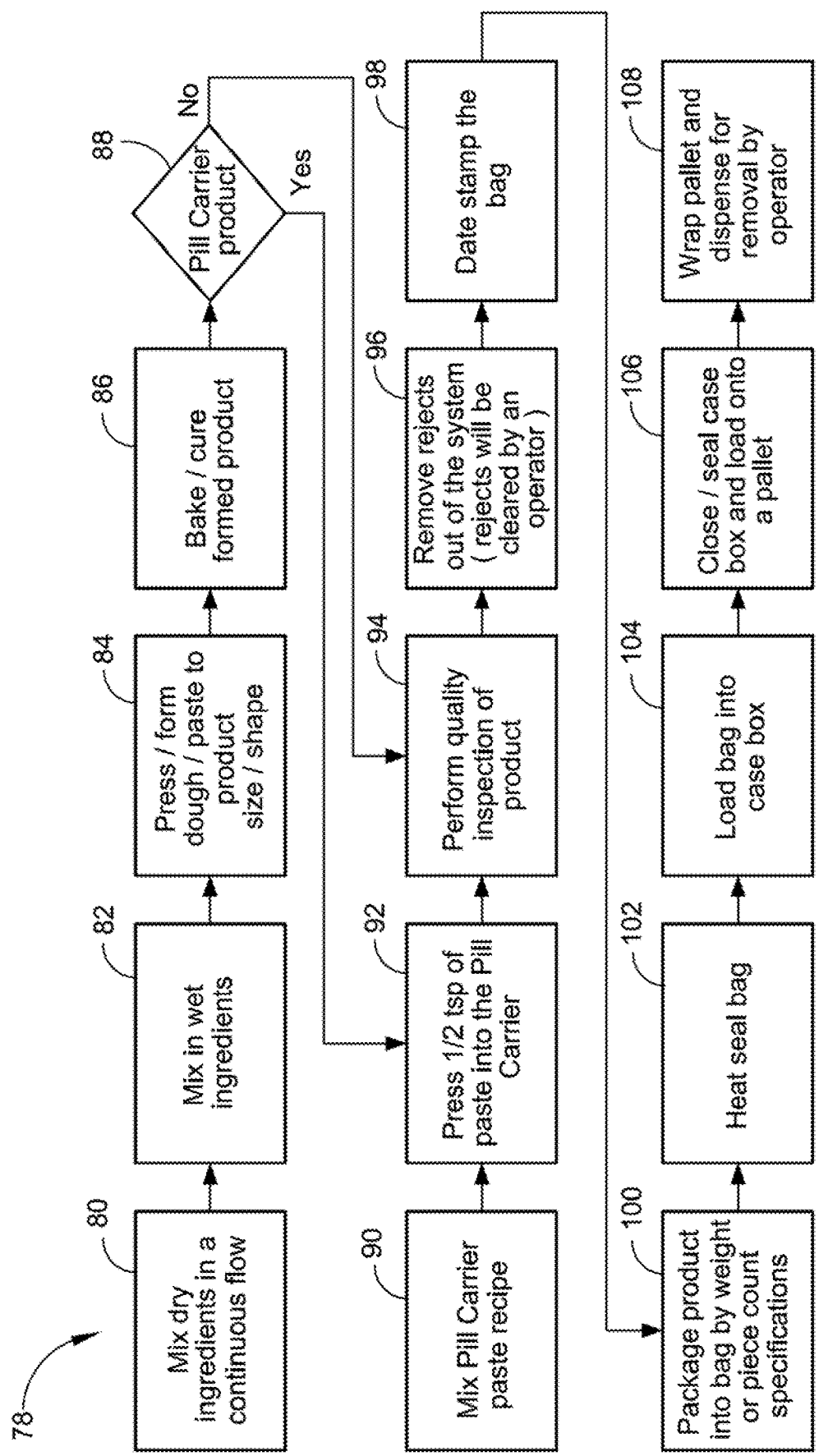
FIG. 6 depicts a block diagram of the second production method.

FIG. 6 depicts a block diagram of the Second production method 78 where Mix dry ingredients in a continuous flow 80 then Mix in wet ingredients 82 and Press/form dough/paste to product size/shape 84 and Bake/cure formed product 86. Transfer to Pill carrier product 88 with YES to Press ½ tsp of paste into the pill carrier 92 where Mix pill carrier paste recipe 90 has been inserted. Next is Perform quality inspection of product 94 then Remove rejects out of the system (rejects will be cleared by an operator) 96 then Date stamp the bag 98 to transfer Package product into bag by weight or piece count specifications 100. Heat seal bag 102 then Load bag into case box 104 then Close/seal case box and load onto a pallet 106 and Wrap pallet and dispense for removal by operator 108.

Figure 7:
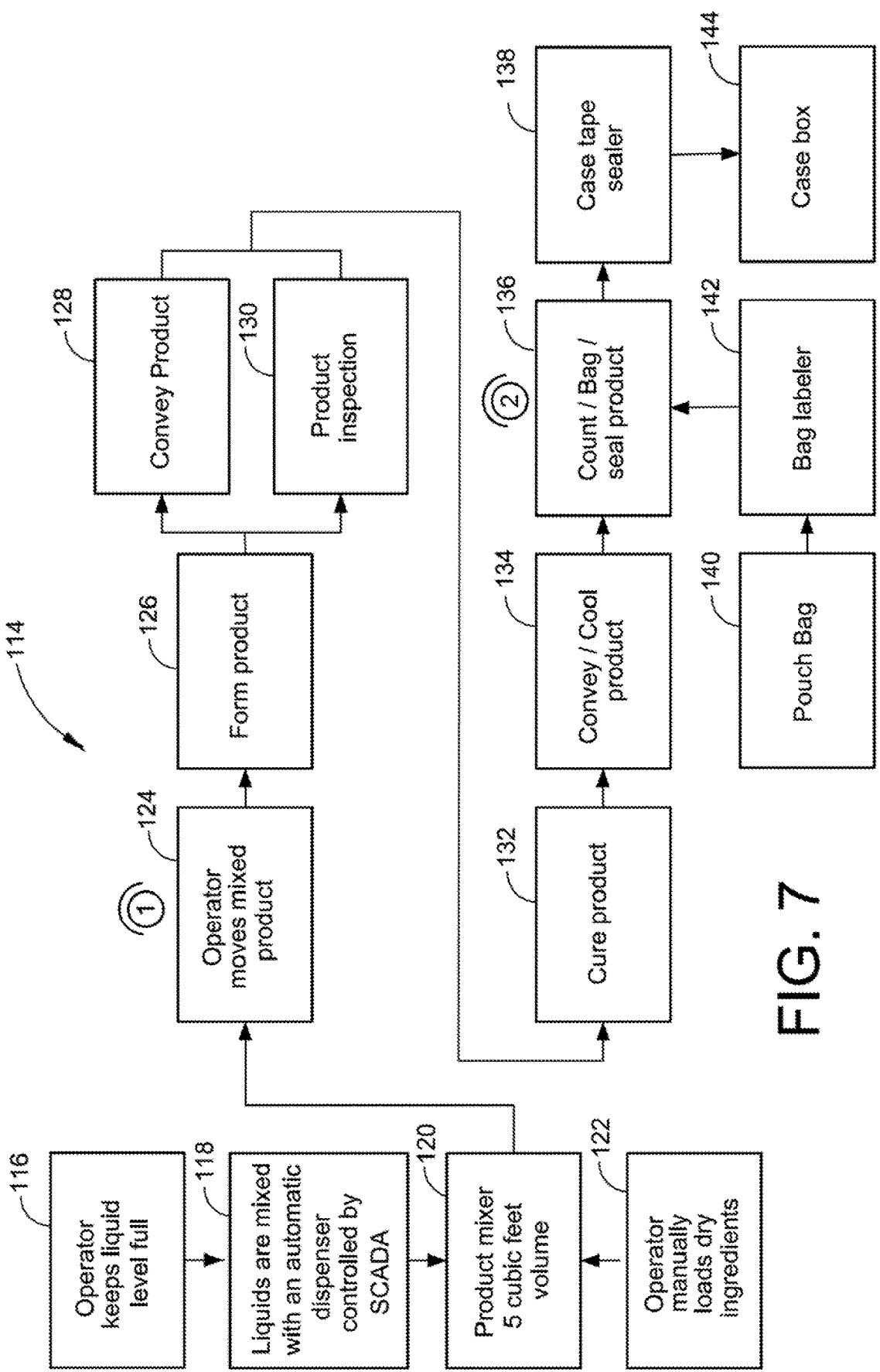
FIG. 7 depicts a block diagram of the third production method.

FIG. 7 depicts a block diagram of the Third production method 114 where Operator keeps liquid level full 116 and Liquids are mixed with an automatic dispenser controlled by SCADA 118 to Product mixer 5 cubic feet volume 120 where Operator manually loads dry ingredients 122 to additionally be inserted into Product mixer 5 cubic feet volume 120. Next Operator moves mixed product 124 to Form product 126 where it either goes to Convey product 128 or Product inspection 130. From those locations it will go to Cure product 132, and Convey/cool product 134 and Count/bag/seal product 136. Pouch bag 140 enters Bag labeler 142 and into Count/bag/seal product 136 to Case tape sealer 138 and Case box 144.

Figure 8A:
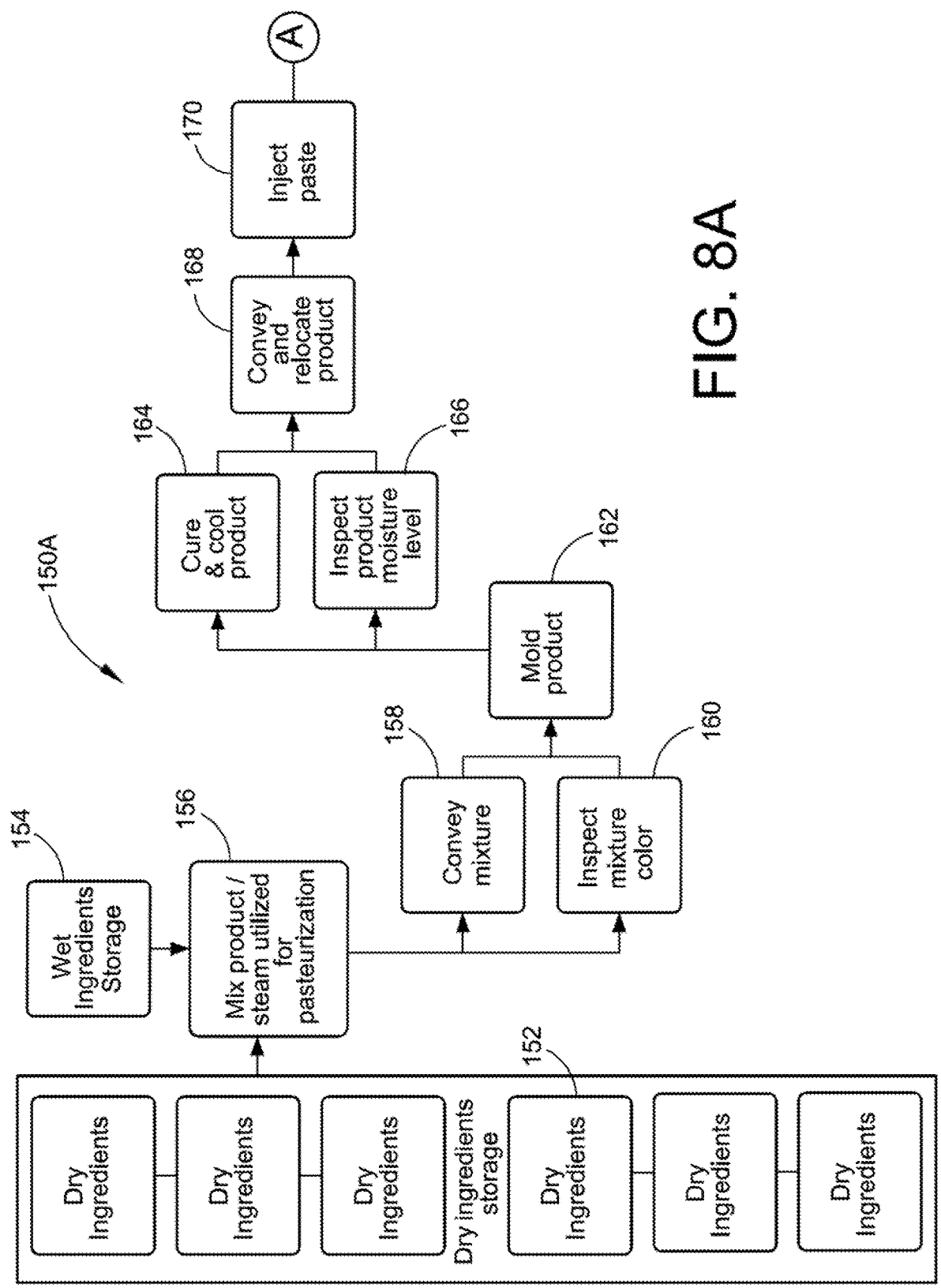
FIG. 8A depicts a block diagram of the first section of the forth production method.

FIG. 8A depicts a block diagram of the first section of the Forth production method 150A where the Dry Ingredients in the Dry ingredients' containers 152 where the Mix product/steam utilized for pasteurization 156 with Wet ingredients storage 154 introduced. Material from the Mix product/steam utilized for pasteurization 156 is distributed between Convey mixture 158 and Inspect mixture color 160 and sent to Mold product 162 where it is then distributed to Cure and cool product 164 and Inspect product moisture level 166 next to Convey and relocate product 168 and Inspect paste 170. The process is transferred between A on page 5/10 to A on page 6/10.

Figure 8B:
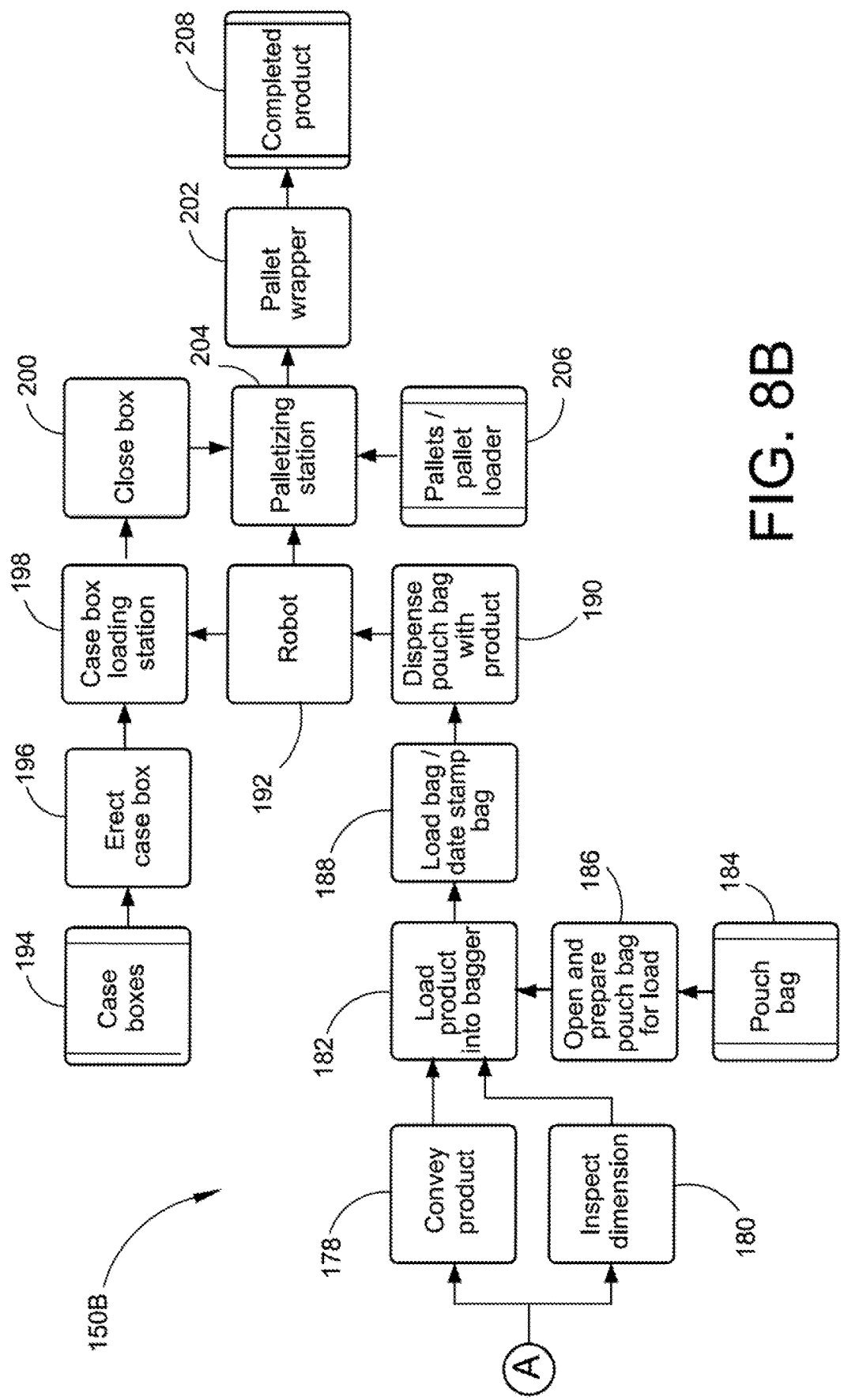
FIG. 8B depicts a block diagram of the second section of the forth production method.

FIG. 8B depicts a block diagram of the second section of the forth production method 150B where A indicates the connection from the A on page 5/10 where the product is distributed between Convey product 178 and Inspect dimension 180 and both lead to Load product in bagger 182 where Pouch bag 184 and Open and prepare pouch bag for load 186 connect. Load product in bagger 182 then connects to Load bag/date stamp bag 188 and Dispense pouch bag with product 190 where it is passed to Robot 192 to go to either Palletizing station 204 or Case box loading station 198 that has received Case boxes 194 and Erect case box 196. Case box loading station 198 additionally goes to Close box 200 that then goes to Palletizing station 204 that has received Pallets/pallet loader 206. Palletizing station 204 sends product to Pallet wrapper 202 then Completed product 208.

Figure 9:
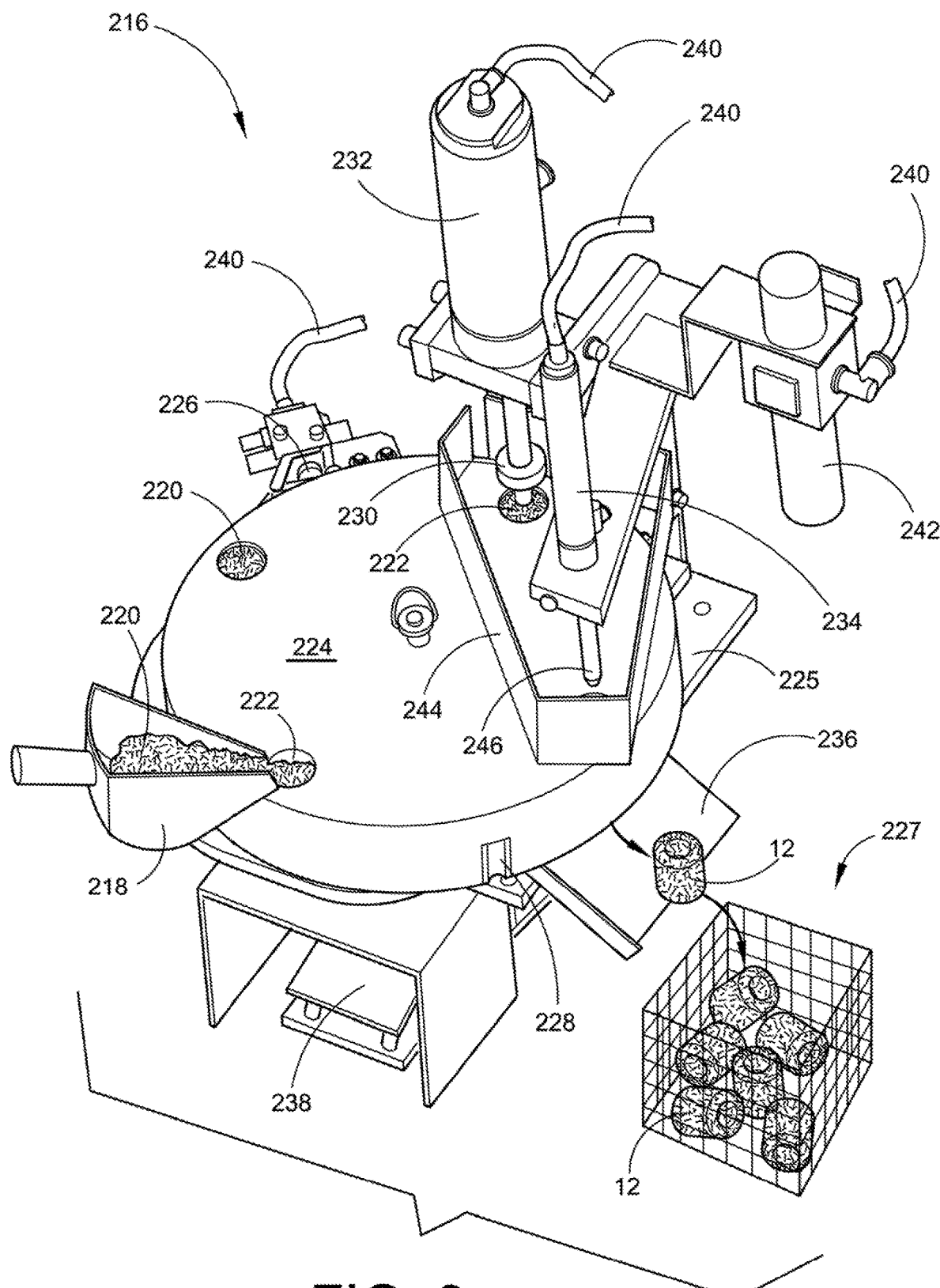
FIG. 9 depicts a perspective view of the commercial pneumatic press modified to produce the hollow cylinder cup style Pill and Paste Carrier.

FIG. 9 depicts a perspective view of the Commercial pneumatic press 216 modified to produce the hollow cylinder style Pill and Paste Carrier 12 or disk style Pill and Paste Carrier 16. A Scoop 218 inserts the disk style Pill and Paste Carrier Psyllium mixture 220 into one of the disk style Pill and Paste Carrier Small psyllium wheel cavities 222 in the Rotatable disk style Pill and Paste Carrier Psyllium wheel 224 that is supported by the means of the Pneumatic press table 225. The Pneumatic indexing mechanism 226 registers the rotatable disk style Pill and Paste Carrier Psyllium wheel 224 in position by the means of four Indentions 228 on the side of the rotatable disk style Pill and Paste Carrier Psyllium wheel 224. When the disk style Pill and Paste Carrier Psyllium filled cavity 222 is positioned under the Small pressure forming head 230 of the Large pneumatic cylinder 232 of pneumatic press 216, it translates down to form the pill and paste carrier 12 at the same time the Small pneumatic cylinder 234 blows the formed pill carrier 12 out of the Small psyllium wheel cavity 222 of the rotatable Psyllium wheel 224 and the finished pill carrier 12 will drop out on the Unloading tray 236 and fall into a holding basket 227. The operator rotates the rotatable disk style Pill and Paste Carrier Psyllium wheel 224 by the means of stepping on the pneumatic Foot peddle actuator 238. The pneumatic press 216 operates by the means of compressed air through Air lines 240 that connect through the Moisture trap 242. A Safety guard 244 encloses the small pressure forming head 230 and the Air nozzle 246 of the small pneumatic cylinder 234.

Figure 10:
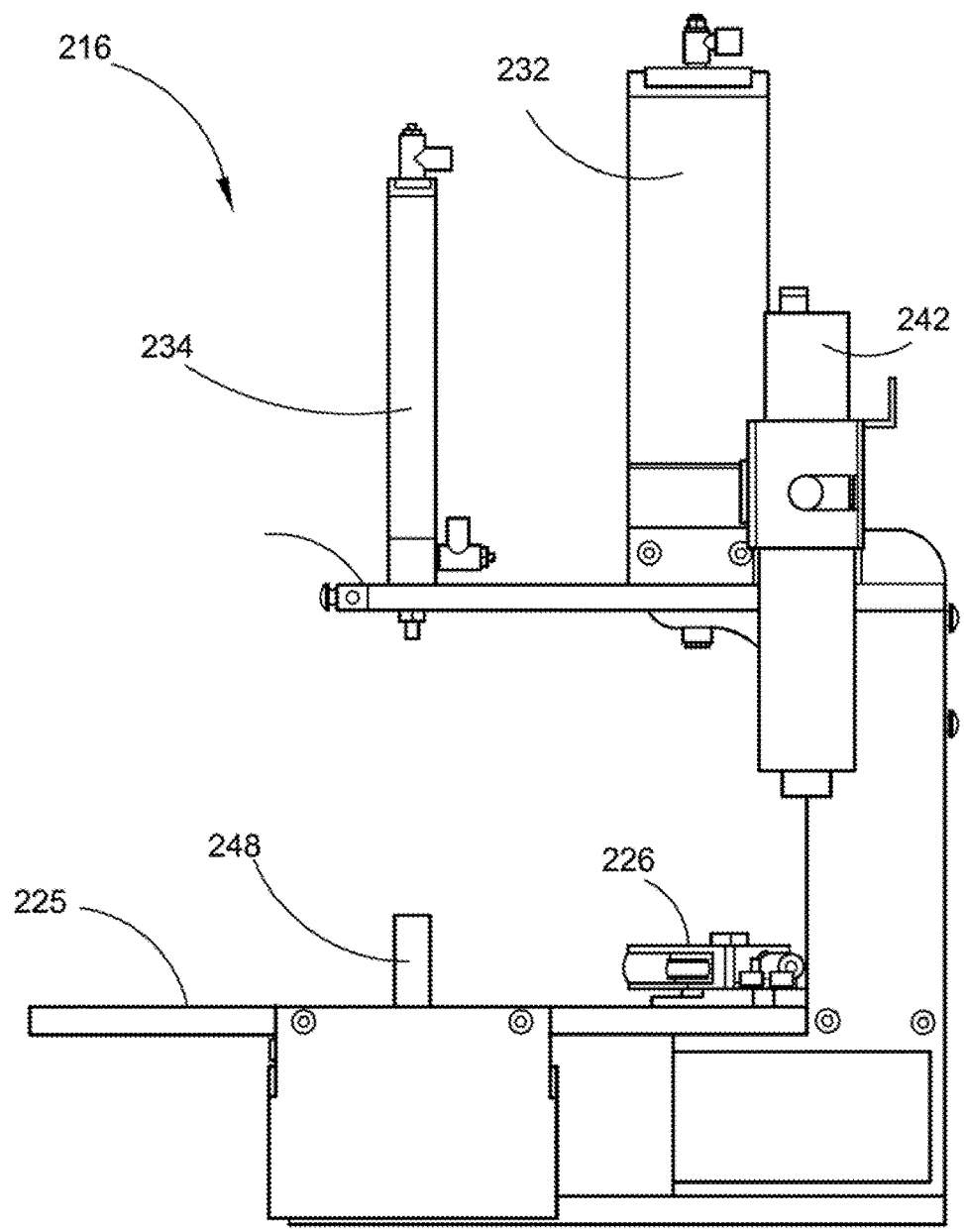
FIG. 10 depicts a side view of the commercial pneumatic press modified to produce the hollow cylinder cup style Pill and Paste Carrier.

FIG. 10 depicts aside view of the Commercial pneumatic press 216 modified to produce the hollow cylinder style 12 or disk style Pill and Paste Carrier 16 with the Small pneumatic cylinder 234, Large pneumatic cylinder 232 and Moisture trap 242. The Spindle 248 extends out of the Pneumatic press table 225 where the disk style Pill and Paste Carrier Psyllium wheel 224 rotates.

Figure 11:
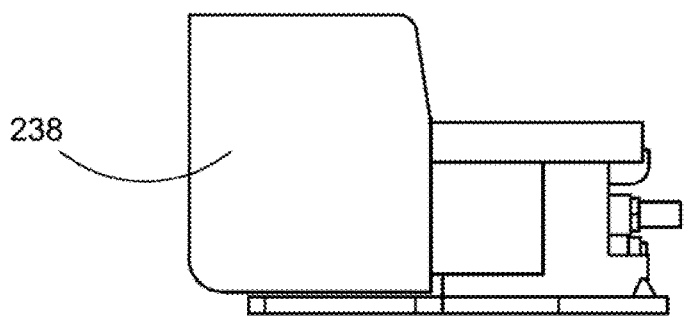
FIG. 11 depicts a side view of the foot peddle actuator to operate the commercial pneumatic press used to produce the hollow cylinder cup style Pill and Paste Carrier.

FIG. 11 depicts a side view of the Foot peddle actuator 238 to operate the Commercial pneumatic press 216 used to produce the Pill and Paste Carrier 12 or disk style Pill and Paste Carrier 16.

Figure 12:
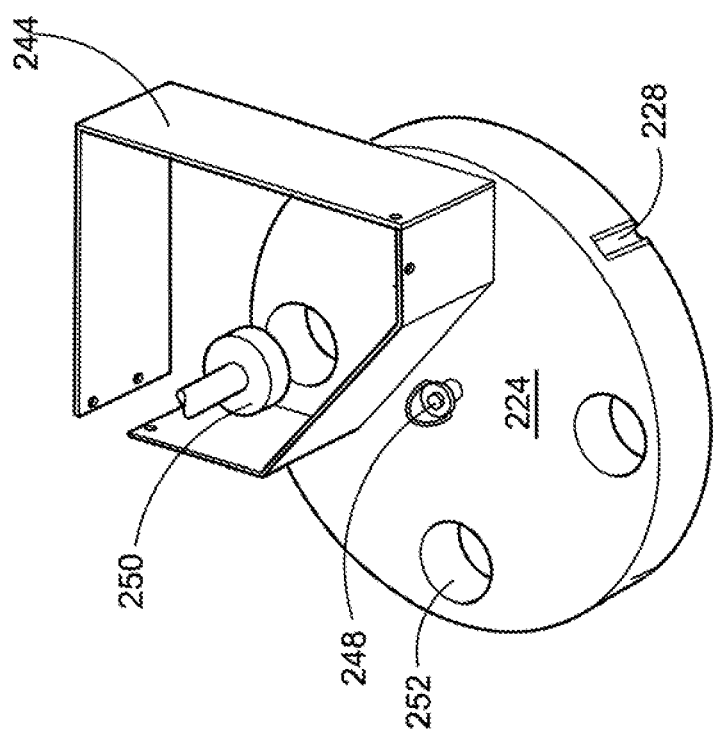
FIG. 12 depicts a perspective view of the rotating psyllium disk style Pill and Paste Carrier wheel with a safety guard and a large round psyllium disk style Pill and Paste Carrier press tool.

FIG. 12 depicts a perspective view of the rotatable disk style Pill and Paste Carrier 16 Psyllium wheel 224 with a Safety guard 244 and the Large round disk style Pill and Paste Carrier psyllium disk press tool 250.

Figure 13:
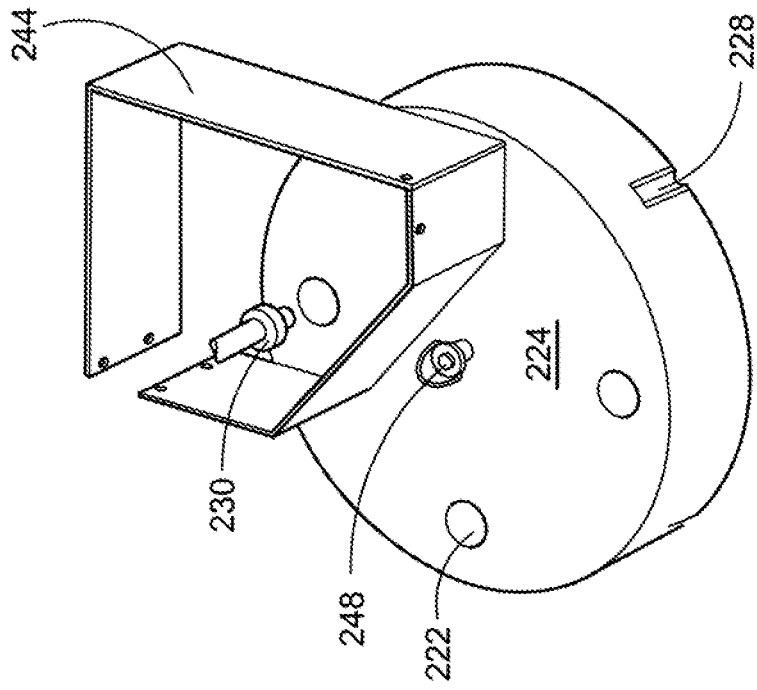
FIG. 13 depicts a perspective view of the rotating psyllium disk style Pill and Paste Carrier wheel with a safety guard and a small round psyllium disk style Pill and Paste Carrier pill carrier press tool.

FIG. 13 depicts a perspective view of the rotatable hollow cylinder style Pill and Paste Carrier 12 wheel 224 with a Safety guard 244 and a small round hollow cylinder style Pill and Paste Carrier pressure forming head 230.

FIG. 14 depicts a perspective bottom view of the rotatable disk style Pill and Paste Carrier 16 psyllium wheel 224.

FIG. 15 depicts a plan view of the bottom of the rotatable disk style Pill and Paste Carrier 16 Psyllium wheel 224.

FIG. 16 depicts a plan view of the top of the rotatable disk style Pill and Paste Carrier 16 Psyllium wheel 224.

FIG. 17 depicts a section view of the rotatable disk style Pill and Paste Carrier 16 Psyllium wheel 224 at one of the rotational indexing Indentions 228.

FIG. 18 depicts a cross section of the rotatable disk style Pill and Paste Carrier 16 Psyllium wheel 224.

Example 1—Preferred Carrier Formulations

The following are examples of preferred Pill and Paste Carrier Formulations by volume:

Top Preferred Formulation #1

| | |
|---|---|
| High Grade Alfalfa | 2.5 lbs. 30 Cups |
| Beet Pulp | ½ cup |
| Fenugreek Powder | ½ Cup |
| Water | 9 Cups |
| Flour | 5½ Cups |
| Dehydrate | 120 degrees F. for 14 hrs. |

Preferred Formulation #2

| | |
|---|---|
| High Grade Alfalfa | 2.5 lbs. 30 Cups |
| Beet Pulp | ½ cup |
| Long and Lush | ½ Cup |
| Water | 8 Cups |
| Flour | 5½ Cups |
| Dehydrate | 120 degrees F. for 14 hrs. |

Preferred Formulation #3

| | |
|---|---|
| High Grade Alfalfa | 2.5 lbs. 30 Cups |
| Beet Pulp | ½ cup |
| Long and Lush | ½ Cup |
| Water | 8 Cups |
| Flour | 5½ Cups |
| Dehydrate | 120 degrees F. for 14 hrs. |

Preferred Formulation #4

| | |
|---|---|
| High Grade Alfalfa | 2.5 lbs. 30 Cups |
| Beet Pulp | ½ cup |
| Long and Lush | 1 Cup |
| Water | 8 Cups |
| Flour | 4 Cups |
| Dehydrate | 115 degrees F. for 10 hrs. |

Preferred Formulation #5

| | |
|---|---|
| High Grade Alfalfa | 2.5 lbs. 30 Cups |
| Beet Pulp | ½ cup |
| Long and Lush | 1 Cup |
| Water | 8 Cups |
| Flour | 4 Cups |
| Dehydrate | 115 degrees F. for 10 hrs. |

Preferred Reformulation #6

| | |
|---|---|
| High Grade Alfalfa | 1 lb. 12 cups |
| Beet Pulp | ½ cup |
| Long and Lush | ½ cup |
| 1 bottle of water | (16.9 oz.) |
| Flour | 1½ cup |
| Dehydrate | 115 degrees F. for 10 hrs. |

Preferred Reformulation #7

| | |
|---|---|
| High Grade Alfalfa | 2.5 lbs. 30 Cups |
| Beet Pulp | ¼ cup |
| Long and Lush | 1 Cup |
| Water | 8 Cups |
| Flour | 4 Cups |
| Dehydrate | 115 degrees F. for 10 hrs. |

Preferred Reformulation #8

| | |
|---|---|
| High Grade Alfalfa | 2 lbs. 24 cups |
| Beet Pulp | ½ lbs. 2% Finished |
| Bentonite | 2 oz. |
| Long and Lush | 2 oz. |
| Dehydrate | 105 degrees F. for 10 hrs. |

Preferred Reformulation #9

| | |
|---|---|
| High Grade Alfalfa | 2 lbs. 24 cups |
| Molasses | 1 Cup 2% Finished |
| Beet Pulp | ½ lbs. |
| Bentonite | 1 Cup |
| Long and Lush | 2 oz. |
| 5 cups of water | |
| Dehydrate | 105 degrees F. for 10 hrs. |

Preferred Reformulation #10

| | |
|---|---|
| High Grade Alfalfa | 1 lb. 12 cups (Brown Arbocel RP 80) |
| Beet Pulp | ¼ cup |
| Long and Lush | 2 oz. |
| 1 bottle of water | (16.9 oz.) |
| Premixed Cellulose | |
| Dehydrate | 105 degrees F. for 14 hrs. |

Preferred Reformulation #11

| | |
|---|---|
| High Grade Alfalfa | 1 lb. 12 cups |
| Beet Pulp | ¼ cup |
| Long and Lush | 2 oz. |
| 1 bottle of water | (16.9 oz.) |
| 2 Cups Premixed Cellulose(White Arbocel BWW 40) | |
| 5 oz. molasses | |
| Dehydrate | 105 degrees F. for 14 hrs. |

Preferred Reformulation #12

| | |
|---|---|
| High Grade Alfalfa | 1 lb. 12 cups |
| Beet Pulp | ¼ cup |
| Fenugreek Powder | 2 tablespoons |
| 1 bottle of water | (16.9 oz.) |
| Premixed Cellulose (Brown Arbocel RP 80) | 3 TBS |
| Flour | 2 Cups |
| Dehydrate | 115 degrees F. for 10 hrs. |

Preferred Reformulation #13

| | |
|---|---|
| High Grade Alfalfa | 1 lb. 12 cups |
| Beet Pulp | ¼ cup |
| Long and Lush | 2 tablespoons |
| 1 bottle of water | (16.9 oz.) |
| Premixed Cellulose (Brown Arbocel RP 80) | 3 TBS |
| Flour | 2 Cups |
| Molasses | ½ cup |
| Water | 1 Cup |
| Dehydrate | 115 degrees F. for 10 hrs. |

Preferred Reformulation #14

| | |
|---|---|
| High Grade Alfalfa | 1 lb. 12 cups |
| Beet Pulp | ¼ cup |
| Long and Lush | 2 tablespoons |
| 1 bottle of water | (16.9 oz.) |
| Premixed Cellulose (Brown Arbocel RP 80) | 3 TBS |
| Molasses | ½ cup |
| Water | 1 Cup |
| Dehydrate | 115 degrees F. for 10 hrs. |

Preferred Reformulation #15

| | |
|---|---|
| High Grade Alfalfa | 1 lb. 12 cups |
| Beet Pulp | ¼ cup |
| Long and Lush | 2 tablespoons |
| 1 bottle of water | (16.9 oz.) |
| Premixed Cellulose (Brown Arbocel RP 80) | 0 |
| Flour | 2 Cups |
| Molasses | ½ cup |
| Water | 1 Cup |
| Dehydrate | 115 degrees F. for 10 hrs. |

Preferred Reformulation #16

| | |
|---|---|
| High Grade Alfalfa | 1 lb. 12 cups |
| Beet Pulp | ¼ cup |
| Long and Lash | 2 tablespoons |
| 1 bottle of water | (16.9 oz.) |
| Flour | 1 cup Very dry - 0% moisture |
| Molasses | ½ cup Lighter with less flour. |
| Dehydrate | 115 degrees F. for 10 hrs. |

Preferred Reformulation #17

| | |
|---|---|
| High Grade Alfalfa | 1 lb. 12 cups |
| Beet Pulp | ¼ cup |
| Long and Lush | 4 tablespoons |
| 1 bottle of water | (16.9 oz.) |
| Flour | 1 cup |
| Dehydrate | 115 degrees F. for 10 hrs. |

Preferred Reformulation #18

| | |
|---|---|
| High Grade Alfalfa | 1 lb. 12 cups |
| Beet Pulp | ½ cup |
| Long and Lush | ½ cup |
| 1 bottle of water | (16.9 oz.) |
| Flour | 1 cup |
| Dehydrate | 115 degrees F. for 10 hrs. |

Preferred Reformulation #19 (Immune Booster)

| | |
|---|---|
| High Grade Alfalfa | 2.5 lbs. 30 Cups |
| Beet Pulp | ½ cup |
| Fenugreek Powder | ½ Cup |
| Immune Support | 1 cup |
| Water | 9 Cups |
| Flour | 5½ Cups |
| Dehydrate | 120 degrees F. for 14 hrs. |

Preferred Reformulation #20

| | |
|---|---|
| | 10 lb. |
| High Grade Alfalfa | 8 lbs. less than 1% Moisture |
| Beet Pulp | 2 lbs. 105 @ 14 Hrs. |
| Long and Lush | 1 oz. 2 Tablespoons |
| Zeolite | 7 oz. 14 tablespoons |
| Water | 7 cups |
| Canola Oil | 1 cup |
| Dehydrate | 105 degrees F. for 14 hrs. |

Preferred Reformulation #21

| | |
|---|---|
| High Grade Alfalfa | 8 lbs. |
| Beet Pulp | 2 lbs. |
| Long and Lush | 1 oz. 2 Tablespoons |
| Zeolite | 3 oz. 6 tablespoons |
| Water | 7 cups |
| Canola Oil | 1 cup |
| Dehydrate | 105 degrees F. for 14 hrs. |

Preferred Reformulation #22

| | |
|---|---|
| High Grade Alfalfa | 4 lbs. |
| Beet Pulp | 1 lbs. |
| Long and Lush | 1 oz. 2 Tablespoons |
| Zeolite | 3 oz. 6 tablespoons |
| Water | 4 cups |
| Molasses | ½ cup |
| Dehydrate | 100 degrees F. for 10 hrs. |

Preferred Reformulation #23

| | 15% Mixture |
|---|---|
| Alfalfa | 2 lbs. 24 cups 4% Finished |
| Beet Pulp | ½ lbs. |
| Long and Lush | 1 oz. |
| Pectin | 8 tablespoons mixed with 4 cups of water |
| Ball Pectin | |
| Dehydrate | 105 degrees F. for 10 hrs |

Preferred Reformulation #24

| | |
|---|---|
| High Grade Alfalfa | 2 lbs. 24 cups |
| Beet Pulp | ½ lbs. |
| Flour | ½ lb. |
| Long and Lust | 2 oz. |
| Pectin | 4.7 oz. mixed with 5 cups of water |
| Ball Pectin | |

Preferred Reformulation #25

| | |
|---|---|
| High Grade Alfalfa | 8 lbs. less than 1% Moisture |
| Beet Pulp | 2 lbs. |
| Long and Lush | 1 oz. 2 Tablespoons |
| Zeolite | 14 Oz. 28 tablespoons |
| Water | 7 cups |
| Canola Oil | 1 cup |
| Dehydrate | 105 degrees F. for 14 hrs. |

Example 2—Pill and Paste Carrier Formulations

The following are examples of preferred Pill and Paste Carrier Formulations by percentage:
Preferred Pill and Paste Carrier Formulation

| Ingredient | % |
|---|---|
| Ground Alfalfa-17% Pro or more | 44.4% |
| White Wheat Flour | 17.8% |
| Ground Molassified COB* | 12.4% |
| Water added to COB | 6.2% |
| Safflower Oil (or Canola Oil) | 1.8% |
| Ground Beet Pulp | 7.1% |
| Water added to beet pulp | 7.1% |
| Sea Salt | 1.8% |
| Long & Lush Flavoring | 0.4% |
| Fenugreek | 0.9% |
| TOTAL | 100.0% |

*COB is a dry COB and not Molassified

Mix the above thoroughly, then add water while mixing to achieve desired consistency.

Example 3—Paste Formulations

The following are examples of preferred Pill and Paste Carrier Paste Formulations by volume:
Preferred Paste Formulation #1

| | |
|---|---|
| Cranberries | 5 Cups |
| Molasses | ¾ Cup |
| Safflower Oil | 2 Cup |

Preferred Paste Formulation #2

| | |
|---|---|
| Cranberries | 5 Cups |
| Molasses | ½ Cup |
| Safflower Oil | 1½ Cup |

Preferred Paste Formulation #3

| | |
|---|---|
| Cranberries | 5 Cups |
| Molasses | ½ Cup |
| Safflower Oil | 2 Cup |

Preferred Paste Formulation #4

| | |
|---|---|
| Cranberries | 4 Cups |
| Molasses | ½ Cup |
| Safflower Oil | 1½ Cup |

With the preferred formulations the following pills, agents or liquids can be delivered using the hollow cylinder style Pill and Paste Carrier 12, or the disk style Pill and Paste Carrier 16: medications of all kinds, probiotics, pre-biotics, psyllium, anti-diuretics, biotin, anti-oxidants, antibiotics, electrolytes, omega-3, DHA and EPA, bone health agents, hoof and coat health agents, fly and pest supplements, vitamins and minerals, digestive health agents, joint health agents, feed supplements, CBD (cannabidiol), herbs, hemp, over-the-counter sedatives, and peanut butter paste, to name a few. Being able to have your pet, livestock, horse, or donkey take these medicines and agents will have a significant bodily effect on the animal and the health and wellness of the animal will be greatly enhanced.

Example 4—Psyllium Infusion

The following is an example of infusing a health agent into the Pill and Paste Carrier Paste formulations: psyllium. Psyllium is a form of fiber made from the husks of the *Plantago ovata* plant's seeds. It sometimes goes by the name ispaghula. It's most commonly known as a laxative. However, research shows that taking psyllium is beneficial to many parts of the human or animal body, including the heart and the pancreas. Psyllium is a bulk-forming laxative. This means it soaks up water in your gut and makes bowel movements" much easier. It also helps promote regularity without increasing flatulence. It can be used as a one-off to ease constipation, or it can be added to your diet to help promote regularity and overall digestive health. People with irritable bowel syndrome and Crohn's disease are all too familiar with the banes of the bathroom. The results of studies on psyllium's effectiveness in treating these conditions are still mixed. Psyllium is a prebiotic—a substance needed for healthy colonies of probiotics to grow in the gut. A healthy colony of good bacteria in the digestive system is essential for healthy immune function. Your body is better able to tight infection, reduce inflammation, and maintain healthy tissue and cells.

Some research has shown that consuming 7.9 grams of psyllium per day (plus or minus 3.6 grams) with probiotics is a safe and effective way to treat Crohn's disease. However, other results show soluble fiber like psyllium can make symptoms worse for some people. Besides keeping your bowel movements regular and managing a chronic condition, psyllium has the ability to soften your stool. This can come in handy with short-term ailments, such as constipation. Used in this way, it can prevent complications of constipation, such as hemorrhoids and anal fissures. Preliminary research shows that psyllium may help with the painful symptoms associated with these conditions. Since there is no real scientific consensus, talk to your doctor to see if psyllium could help you.

The benefits to horses and other livestock is that psyllium can help clear sand from digestive system. Livestock and horses that ground graze or are fed on the ground in the western United States are most effected. This is most relevant in areas and geographies where animals are fed on the ground where sand is prevalent, such as Southern California, Arizona, New Mexico, Texas, Oklahoma, etc. When the Pill and Paste Carrier of the present invention is infused with psyllium, feeding this aids in digestive function for those horses and livestock fed on the ground in the above mentioned areas, and any sandy soil areas throughout the world. In this way, the uptake of psyllium in the Pill and Paste Carrier aids in digestion, clears sand, and has an overall beneficial effect on the animal's body and health.

Example 5—Various Medications, Nutritional Agents and Health Benefiting Supplements By way of example, it is anticipated that the Pill and Paste Carrier of the present invention can be used to deliver numerous varying doses of nutritional agents as well as differing health benefitting supplements. Some of the anticipated uses, along with informational websites, are as follows:

Cannabidiol also known as CBD—1000% hemp based added to paste or form. CBD is known for anti-inflammatory and anti-anxiety properties. It is frequently used in animal products and treats. See: https://www.wbir.com/article/news/local/treats-with-cbd-oil-a-hit-with-owners-of-anxious-pets/51-589714818

Antibiotic or fortification delivery for emaciated animals through being mixed in paste. Benefit to the body through effective drug delivery of less palatable medications. See: https://www.nytimes.com/2013/01/31/health/antibiotics-can-save-lives-of-severely-malnourished-children-studies-find.html Oral agent delivery system for flea and tick oral medication to an animal. Benefits include animal becoming flea or tick free. See: https://www.americanveterinarian.com/news/product-news-new-flea-and-tick-preventive-granted-fda-approval Omega 3 and Omega 6 added to paste for skin, coat and heart health. See: https://thehorse.com/110549/improving-dry-equine-skin-and-coats-with-nutrition/

Biotin for hoof and hair/coat health mixed into paste or form. Biotin is used in human and animal populations for hoof, skin and coat health. See: https://thehorse.com/19448/horse-hoof-health-and-nutrition-balance-is-key/

Electrolytes and salt mixed into paste or form. Benefit is replacing minerals that are lost during physical activity. See: https://equimanagement.com/news/top-five-horse-management-tips-during-heat-and-humidity Chondroitin sulfate and Glucosamine mixed into paste for joint health and to support aging. See: https://www.farmforum.net/farm_forum/caring-for-your-senior-horse/article_416b6a42-35f4-53c4-b0b5-f814803f79a6.html Conjugated linoleic acid (CLA) added into paste or form. CLA is in research as having potential benefits towards inflammation reduction and decreasing plasma arachidonic acid. See: https://www.ncbi.nlm.nih.gov/pubmed/22829604, https://thehorse.com/160534/can-a-supplement-help-delay-arthritis-onset-in-young-horses/

Oral cancer medication mixed into paste, delivery of oral suspension medication. See: https://www.wedgewoodpetrx.com/items/othercancer/chlorambucil-prednisone-oral-oil-suspension.html?no_redirect=true Dental gel delivery through mixing dental oral cleansing gels into paste. Oral cleansing gel is used for cleaner and freshener in the pet/livestock market. See: https://addison-labs.com/product/maxiguard-oral-cleansing-gel/

Fiber delivery cellulose/psyllium mixed into form for fiber delivery. Fiber additions to diet is often used for gastrointestinal health needs. See: http://www.kadampsyllium.com/d-husk-seed.html Essential micro and macro minerals, vitamins and amino acid delivery through form or paste. Benefit to assure uptake of essential vitamins and minerals. See: https://www.smartpakequine.com/horse-multivitamin-supplements-13pc Antihistamine delivery through mix in through form or paste. Benefit reduction in allergies. See: https://horsesidevetguide.com/drv/Treatment/49/antihistamines-injectable-or-oral/

The Pill and Paste Carrier 10 in a hollow cylinder style embodiment 12 and a disk style embodiment 16, shown in the drawings and described in detail herein disclose arrangements of elements of particular recipe, fabrication processes and configuration for illustrating preferred embodiments of structure and method of design of the present application. It is to be understood, however, that elements of different construction and configuration and other arrangements thereof, other than those illustrated and described may be employed for providing a Pill and Paste Carrier 10 in a hollow cylinder style embodiment 12 and a disk style embodiment 16, in accordance with the spirit of this disclosure, and such changes, alternations and modifications as would occur to those skilled in the art are considered to be within the scope of this design as broadly defined in the appended claims.

While certain embodiments of the inventions have been described, these embodiments have been presented by way of example only, and are not intended to limit the scope of the disclosure. Indeed, the novel methods and systems described herein may be embodied in a variety of other forms. Furthermore, various omissions, substitutions and changes in the systems and methods described herein may be made without departing from the spirit of the disclosure. For example, one portion of one of the embodiments described herein can be substituted for another portion in another embodiment described herein. The accompanying claims and their equivalents are intended to cover such forms or modifications as would fall within the scope and spirit of the disclosure. Accordingly, the scope of the present inventions is defined only by reference to the appended claims.

Features, materials, characteristics, or groups described in conjunction with a particular aspect, embodiment, or example are to be understood to be applicable to any other aspect, embodiment or example described in this section or elsewhere in this specification unless incompatible therewith. All of the features disclosed in this specification (including any accompanying claims, abstract and drawings), and/or all of the steps of any method or process so disclosed, may be combined in any combination, except combinations where at least some of such features and/or steps are mutually exclusive. The protection is not restricted to the details of any foregoing embodiments. The protection extends to any novel one, or any novel combination, of the features disclosed in this specification (including any accompanying claims, abstract and drawings), or to any novel one, or any novel combination, of the steps of any method or process so disclosed.

Furthermore, certain features that are described in this disclosure in the context of separate implementations can also be implemented in combination in a single implementation. Conversely, various features that are described in the context of a single implementation can also be implemented in multiple implementations separately or in any suitable subcombination. Moreover, although features may be described above as acting in certain combinations, one or more features from a claimed combination can, in some cases, be excised from the combination, and the combination may be claimed as a subcombination or variation of a subcombination.

Moreover, while operations may be depicted in the drawings or described in the specification in a particular order, such operations need not be performed in the particular order shown or in sequential order, or that all operations be performed, to achieve desirable results. Other operations that are not depicted or described can be incorporated in the example methods and processes. For example, one or more additional operations can be performed before, after, simultaneously, or between any of the described operations. Further, the operations may be rearranged or reordered in other implementations. Those skilled in the art will appreciate that in some embodiments, the actual steps taken in the processes illustrated and/or disclosed may differ from those shown in the figures. Depending on the embodiment, certain of the steps described above may be removed, others may be added. Furthermore, the features and attributes of the specific embodiments disclosed above may be combined in different ways to form additional embodiments, all of which fall within the scope of the present disclosure. Also, the separation of various system components in the implementations described above should not be understood as requiring such separation in all implementations, and it should be understood that the described components and systems can generally be integrated together in a single product or packaged into multiple products.

For purposes of this disclosure, certain aspects, advantages, and novel features are described herein. Not necessarily all such advantages may be achieved in accordance with any particular embodiment. Thus, for example, those skilled in the an will recognize that the disclosure may be embodied or carried out in a manner that achieves one advantage or a group of advantages as taught herein without necessarily achieving other advantages as may be taught or suggested herein.

Conditional language, such as "can," "could," "might," or "may," unless specifically stated otherwise, or otherwise understood within the context as used, is generally intended to convey that certain embodiments include, while other embodiments do not include, certain features, elements, and/or steps. Thus, such conditional language is not generally intended to imply that features, elements, and/or steps are in any way required for one or more embodiments or that one or more embodiments necessarily include logic for deciding, with or without user input or prompting, whether these features, elements, and/or steps are included or are to be performed in any particular embodiment.

Conjunctive language such as the phrase "at least one of X, Y, and Z," unless specifically stated otherwise, is otherwise understood with the context as used in general to convey that an item, term, etc. may be either X, Y, or Z. Thus, such conjunctive language is not generally intended to imply that certain embodiments require the presence of at least one of X, at least one of Y, and at least one of Z.

Language of degree used herein, such as the terms "approximately," "about," "generally," and "substantially" as used herein represent a value, amount, or characteristic close to the stated value, amount, or characteristic that still performs a desired function or achieves a desired result. For example, the terms "approximately", "about", "generally," and "substantially" may refer to an amount that is within less than 10% of, within less than 5% of, within less than 1% of, within less than 0.1% of, and within less than 0.01% of the stated amount. As another example, in certain embodiments, the terms "generally parallel" and "substantially parallel" refer to a value, amount, or characteristic that departs from exactly parallel by less than or equal to 15 degrees, 10 degrees, 5 degrees, 3 degrees, 1 degree, or 0.1 degree.

The scope of the present disclosure is not intended to be limited by the specific disclosures of preferred embodiments in this section or elsewhere in this specification, and may be defined by claims as presented in this section or elsewhere in this specification or as presented in the future. The language of the claims is to be interpreted broadly based on the language employed in the claims and not limited to the examples described in the present specification or during the prosecution of the application, which examples are to be construed as non-exclusive.

Further, the purpose of the foregoing abstract is to enable the U.S. Patent and Trademark Office and the public generally, and especially the scientists, engineers and practitioners in the art who are not familiar with patent or legal terms or phraseology, to determine quickly from a cursory inspection the nature and essence of the technical disclosure of the application. The abstract is neither intended to define the invention of the application, which is measured by the claims, nor is it intended to be limiting as to the scope of the invention in any way.

We claim:

1. A method of making a pill and paste carrier for introduce beneficial health agents, comprising the steps of:
   (a) formulating a forage-based mixture containing a binder compound, a flavor enhancing compound and forage;

(b) mixing said forage-based mixture containing a binder compound, a flavor enhancing compound and forage;

(c) adding said forage-based mixture to a press mold;

(d) applying pressure to said mixture added to said press mold to result in a press molded form;

(e) ejecting the resulting press molded forage-based mixture press molded form from the press mold;

(f) dehydrating the ejected press molded form; and (g) filling said press molded form with a beneficial health agent or medication comprising a medication pill or medication paste or a nutritional supplement pill or paste;

wherein said press molded form filled with a medication pill or medication paste or a nutritional supplement pill or paste, and thereby said press molded form facilitates the consumption of said medications and said supplements by livestock, horses, pets and companion animals.

2. The method for making a pill and paste carrier used to introduce beneficial health agents according to claim 1, wherein said press molded form includes a hollow cylinder shaped form.

3. The method for making a pill and paste carrier used to introduce beneficial health agents according to claim 1, wherein said press molded form includes a disk shaped form.

4. The method for making a pill and paste carrier used to introduce beneficial health agents according to claim 2, wherein said press molded hollow cylinder shaped form further includes a non-medicated paste added therein, to enable the insertion of a medication pill to facilitate the consumption of said medication pill by livestock, horses, pets and companion animals.

5. The method for making a pill and paste carrier used to introduce beneficial health agents according to claim 1, wherein said forage-based mixture containing a binder compound, a flavor enhancing compound and forage, includes a legume as the forage.

6. The method for making a pill and paste carrier used to introduce beneficial health agents according to claim 1, wherein said forage-based mixture containing a binder compound, a flavor enhancing compound and forage, includes a grass as the forage.

7. The method for making a pill and paste carrier used to introduce beneficial health agents according to claim 5, wherein said forage includes a legume and said legume is alfalfa.

8. The method for making a pill and paste carrier used to introduce beneficial health agents according to claim 1, wherein said press mold includes a press table, a pneumatically driven press, a pneumatically driven plunger ejector, a rotatable press mold wheel and a foot activated peddle actuator.

9. The method for making a pill and paste carrier used to introduce beneficial health agents according to claim 8, wherein said rotatable press mold includes four or more mold cavities shaped to form hollow cylinder cup shaped pill and paste carriers.

10. The method for making a pill and paste carrier used to introduce beneficial health agents according to claim 1, wherein said rotatable press mold includes four or more mold cavities shaped to form disk shaped pill and paste carriers.

11. The method for making a pill and paste carrier used to introduce beneficial health agents according to claim 1, wherein said formulating a forage-based mixture containing a binder compound includes molasses as the binder.

12. The method for making a pill and paste carrier used to introduce beneficial health agents according to claim 1, wherein said formulating a forage-based mixture containing a flavor enhancing compound includes fenugreek as the flavor enhancing compound.

13. The method for making a pill and paste carrier used to introduce beneficial health agents according to claim 3, wherein said disk shaped form pill and paste carrier is infused with the pre-biotic psyllium.

14. The method for making a pill and paste carrier used to introduce beneficial health agents according to claim 4, wherein said paste added to said hollow cylinder cup shaped form includes a pill, liquid medication, powder medication and health benefiting supplement.

15. The method for making a pill and paste carrier used to introduce beneficial health agents according to claim 4, wherein said paste added to said hollow cylinder cup shaped form includes cranberry.

16. The method for making a pill and paste carrier used to introduce beneficial health agents according to claim 4, wherein said paste added to said hollow cylinder cup shaped form includes safflower oil.

17. A method for administering compounds medications and nutritional supplements to an animal, comprising the steps of:

(a) formulating a forage-based mixture containing a binder compound, a flavor enhancing compound and forage;

(b) mixing said forage-based mixture containing a binder compound, a flavor enhancing compound and forage;

(c) pressing said mixture into a hollow cylinder cup shaped form;

(d) adding a non-medicated paste containing a palatable flavor enhancing substance;

(e) feeding said non-medicated paste filled form to an animal on a regular routine basis, for the purpose of getting the animal used to consuming said non-medicated paste filled form on a regular routine;

(f) adding a compound medication pill, a medication paste or a nutritional supplement to the non-medicated paste, thereby forming a medicated paste; and (g) feeding the animal the hollow cylinder cup shaped form including said medicated paste containing the compound medication pill, medication paste or nutritional supplement; wherein said animal regularly and routinely fed the hollow cylinder cup shaped non-medicated paste filled form will readily uptake the hollow cylinder cup shaped medicated paste filled form which has the compound medication or nutritional supplement added, thereby facilitating the introduction by consumption of a compound medication or nutritional supplement to the animal.

18. A method for administering medications and nutritional supplements to an animal according to claim 17, wherein said forage-based mixture is pressed into a disk shape form.

19. A method for administering medications and nutritional supplements to an animal according to claim 17, wherein said added paste includes cranberries, molasses and safflower oil.

20. A method for administering medications and nutritional supplements to an animal according to claim 18, wherein said disk shaped form is infused with psyllium.

* * * * *